United States Patent [19]

Bernhardt et al.

[11] 4,283,565

[45] Aug. 11, 1981

[54] PROCESS FOR PREPARING BENZYLALCOHOLS

[75] Inventors: Günther Bernhardt, St. Augustin; Gerhard Daum, Cologne, both of Fed. Rep. of Germany

[73] Assignee: Dynamit Nobel AG, Troisdorf, Fed. Rep. of Germany

[21] Appl. No.: 974,468

[22] Filed: Dec. 29, 1978

[30] Foreign Application Priority Data

Dec. 31, 1977 [DE] Fed. Rep. of Germany ....... 2759168
Jun. 9, 1978 [DE] Fed. Rep. of Germany ....... 2825364

[51] Int. Cl.$^3$ .......................................... C07C 29/128
[52] U.S. Cl. ..................... 568/648; 568/584; 568/587; 568/588; 568/637; 568/638; 568/649; 568/650; 568/651; 568/652; 568/705; 568/706; 568/709; 568/710; 568/711; 568/713; 568/715; 568/764; 568/811; 568/812; 560/234; 560/236; 260/465 F; 260/465 H; 260/465 G

[58] Field of Search ............... 568/764, 715, 638, 584, 568/587, 588, 705, 706, 709, 710, 711, 713, 637, 648, 649, 650, 651, 652, 812, 811; 560/234, 236; 260/465 F, 465 H, 465 G

[56] References Cited

U.S. PATENT DOCUMENTS

| | | | |
|---|---|---|---|
| 3,098,093 | 7/1963 | Hagemeyer et al. | 560/234 |
| 3,328,439 | 6/1967 | Hamilton | 560/234 X |
| 3,931,290 | 1/1976 | Bourgau et al. | 560/236 |
| 3,993,699 | 11/1976 | Maeda et al. | 568/715 |
| 4,117,251 | 9/1978 | Kaufhold et al. | 560/236 |
| 4,134,925 | 1/1979 | Petersen et al. | 568/638 X |

FOREIGN PATENT DOCUMENTS

| | | | |
|---|---|---|---|
| 2024948 | 1/1971 | Fed. Rep. of Germany | 560/230 |
| 2534209 | 2/1977 | Fed. Rep. of Germany | |
| 51-48626 | 4/1976 | Japan | 560/236 |
| 51-65725 | 6/1976 | Japan | 560/236 |
| 875999 | 8/1961 | United Kingdom | 560/236 |

*Primary Examiner*—Bernard Helfin
*Attorney, Agent, or Firm*—Sprung, Felfe, Horn, Lynch & Kramer

[57] ABSTRACT

There is described an essentially two step process for the preparation of benzylalcohols including those benzylalcohols having substituents on the benzyene ring by reaction of a substituted or unsubstituted benzyl halide with a formate typically an alkali or alkaline earth metal formate to form the corresponding substituted or unsubstituted benzyl formate. In the second step of the process the benzyl formate is contacted with an alcohol whereby the same is converted into the desired benzylalcohol. Both steps can be performed employing catalysts. Described in the specification is the realization of the desired product in exceptionally high yields in a short period of time whereby the process is characterized by high space-time yields.

48 Claims, No Drawings

PROCESS FOR PREPARING BENZYLALCOHOLS

BACKGROUND OF THE INVENTION

FIELD OF THE INVENTION

This invention relates to the preparation of substituted or unsubstituted benzyl alcohols by reaction of benzyl halides with alkali metal or alkaline earth metal formates at an elevated temperature in the presence of a benzyl formate to the corresponding benzyl alcohol by contacting the benzyl formate with an alcohol suitably in the presence of an esterification catalyst. This invention is concerned with a commercially feasible process which provides high yields of desired substituted or unsubstituted benzyl alcohols at high space-time yields.

Benzyl alcohols, especially the ones substituted in the benzene ring, are valuable intermediates for organic syntheses, i.e., starting substances for the manufacture of the corresponding benzoic aldehydes. Xylyleneglycols and nuclear substituted xylyleneglycols are, for example, starting materials for the manufacture of polyesters and polyurethanes.

Starting from benzylhalides, such as benzylchlorides or -bromides or xylylenedichlorides, two general methods for the preparation of benzyl alcohols or xylyleneglycols are used:

(a) The direct saponification of benzylhalides or xylylenedichlorides with dilute aqueous alkali metal hydroxide- and -carbonate- solutions, and (b) a two-step process consisting of a conversion of benzylhalides as well as xylylenedichloride with alkali metal- or alkaline earth acetates to benzyl acetates as well as xylyleneglycolbisacetates which afterwards are saponified to the corresponding benzyl alcohols as well as glycols.

The method of direct saponification mentioned under (a) has the advantage of being a one-step process. On the other hand, considerable quantities of dibenzyl ether occur generally as by-products, as well as polymers of xylylenedichlorides. Therefore, up to 20% of dibenzyl ether may form during alkaline hydrolysis. (Ullmann, volume 4, page 310.)

According to this procedure, benzyl chlorides, i.e., dimethylbenzylchloride or methoxybenzylchloride substituted in the benzene nucleus by one or more methyl groups or another electronegative group, do not produce the desired alcohol as principal product, but the corresponding dibenzyl ether (German Pat. No. P 11 08 677). In this German patent, a two-step process is described.

One procedes in such a way that one heats up benzylhalides or xylyenedihalides, preferably chlorides with alkali metal or alkaline earth acetate in a concentrated aqueous solution until all halogenmethyl groups are changed to acetoxymethyl groups, and, afterwards, benzyl alcohols or xylyleneglycols are freed through saponification with alkali metal or alkaline earth metal hydroxides.

There is no doubt that the formation of dibenzyl ethers or resin-like products is prevented, but the disadvantage of this procedure resides in that it takes long reaction-times for the formation of acetates in the first reaction-step. It is also disadvantageous that high sodium acetate surpluses must be used, amounting up to six-fold the required quantity, restricting the economy very heavily. Besides, a solvent must be used as a reaction-medium, decreasing the utilization capacity of the reactor.

Saponification has been suggested under increased temperatures and pressure (U.S. Pat. No. 2,939,886), with addition of emulsifiers (U.S. Pat. No. 2,819,319) or saponification under heavy shear agitation (DE-AS No. 16 18 530).

Consequently, all of these measures increase the rate of saponification, but do not stop the formation of dibenzyl ether or resin-like by-products. In order to keep the resin content in the reaction product to a minimum, working in dilute solutions is necessary. Therefore, for example, only xylylenedichloride concentrations of a maximum of 5 to 8 weight percent within the aqueous reaction solutions are possible. Therefore, it follows, that after completed saponification heavily dilute xylyleneglycol solutions result which must be concentrated to a gylcol content of 15 weight percent or, in the case of easily water soluble glycols, must be evaporated until complete dryness in order to isolate the glycols by crystallization or extraction. The evaporation of such large amounts of water is economically unsound and constitutes a disadvantage of the procedure.

According to the process of U.S. Pat. No. 2,939,886, the conversion of xylylenedichloride with alkali acetates is carried out in water at increased temperatures and elevated pressure. The separation of xylyleneglycol is achieved through saponification of its bisacetate. This procedure has the disadvantage of an exceptionally long reaction-time of 11 hours until the completion of the first reaction step, and of low glycol-yields after saponification during the second reaction-step. In addition, an autoclave is necessary for the implementation of the conversion.

According to another process (U.S. Pat. No. 3,993,699) in which these disadvantages are said to be eliminated, xylylenedichloride is reacted with an alkali metal or alkaline earth acetate to xylyleneglycolbisacetate in the presence of an aromatic hydrocarbon as adjuvant and a tertiary amine as catalyst. This bisacetate is saponified with aqueous alkaline lye to xylyleneglycol. After separation of the adjuvant and the catalyst, xylyleneglycol is extracted from the aqueous solution.

This particular procedure shows decisive disadvantages also. The conversion to xyleneglycolbisacetate progresses in a satisfactory way only in the presence of an adjuvant. By using large amounts of the adjuvant, valuable utilization space within the reactor is lost. The starting concentration of xylylenedichloride in the reaction mixture amounts to only 25 to 40 weight percent. In addition, through the dilution effect of the adjuvant, the reaction time is considerably lengthened. Another disadvantage resides in that after saponification, only heavily dilute xylyleneglycol solutions are present with a maximum 16 weight percent glycol as well as an additional 20 weight percent sodium acetate as by-product. In order to isolate the xylyleneglycol by means of extraction, a multi-fold amount of the aqueous solution as extraction medium is necessary, and, in order to regain the sodium acetate from the aqueous solution free of glycol, large amounts of water must be evaporated. Therefore, the economical feasability of this process is unsatisfactory.

Furthermore, a process has been described, wherein benzylbenzoate is formed through conversion of benzylchloride and sodiumbenzoate in large quantities in the presence of tertiary amine used as catalyst. Yet, the literature does not mention anything about the preparation of xylyleneglycolbisbenzoate of the corresponding glycol.

As shown in the comparative example, transferring this reaction to xylylenedichloride is impossible, since a reaction mixture consisting of one mol xylylenechloride and 2 mols sodiumbenzoate can not be stirred. The preparation of xylyleneglycol through bisbenzoate would be economically unsound, since only 40 weight percent of the mol mass consists of the xylyleneglycol component.

Within the DE-OS No. 2 731 259 the preparation of substituted benzylformate in o-position through electron-attracting radicals, such as nitro-, cyane- or halogen-, is discussed, but no reference is given to the preparation of benzyl alcohols. The disadvantage of this well known process residues in that the formation of benzylformates derived from benzylhalide and sodium formate requires large amounts of solvents, such as dimethyl sulfoxide, dimethyl formamide or hexamethylphosphoric acid triamide and that the benzylformates have to be separated from the solvents through the addition of large amounts of water. In this way, the space- time- yield diminishes with the presence of large amounts of solvents. In order to regain the expensive solvents which are soluble with water in unlimited amounts, large quantities of water have to be evaporated, making the process complicated and economically unsound.

The presented invention is addressed to the problem of supplying an economically improved procedure for the preparation of benzyl alcohols and benzyl alcohols substituted in the benzene ring, for example xylyleneglycols, which can be carried out from a commercial point of view without large structural apparatus and which provides good yields within short reaction times.

SUMMARY OF THE INVENTION

The foregoing objects are fulfilled in accordance with the invention by contacting a benzylhalide especially where the halide is chlorine and/or bromine or a substituted benzylhalide such as xylylenedihalide with an alkali metal or alkaline earth metal formate and subjecting the resultant benzyl formate so formed to transesterification in order to form benzyl alcohols or xylyleneglycols, as the case may be.

Fundamentally, the conversion to benzyl formate as well as substituted benzyl formates can be achieved without the use of an inert solvent for the substituted or unsubstituted benzylhalide and/or the admixed alkali metal or alkaline earth formate.

The conversion without the use of a solvent takes place in an advantageous manner, namely, in the heterogenous phase whereby the alkali metal and/or alkaline earth metal formate constitute the solid phase and the benzylhalide or xylylenehalide constitute the liquid phase.

The conversion occurs at or above the melting point of the admixed halide, but below the disintegration temperature of the developing or admixed formates or admixed halides and below the melting points of the alkali metal and/or alkaline earth metal formates. In general, during preparation of benzyl formates or xylyleneglycolbisformates one works with temperatures in the area of 100° to 250° C., preferably between 110° and 200° C. Depending on the reaction components, temperatures may range below or above the range mentioned above.

According to the invention, unsubstituted as well as substituted benzyl chlorides and/or -bromides in singular or multiple form (also nuclearly-substituted) are suitable for the conversion with alkali- and/or alkaline earth formates.

For example, nuclear-substituted benzylhalides are such as shown in the general formula

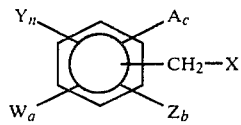

where the substituents represent are:
Y = halogen, especially Cl or Br and/or alkyl groups, (n = 0 to 5, preferably 0 to 2),
W = $CH_2$—X, (a = 0 to 5, preferably 0 to 2)
Z = OH and/or alkoxy and/or phenoxy groups (b = 0 to 3, preferably 0 to 2),
A = nitro groups and/or nitrile groups (c = 0 to 2) whereby a + b + n + c = 1 to 5, preferably 1 to 3 and where X represents chlorine or bromide.

Considered as alkyl groups or alkoxy groups are those with from 1 to 8, preferably 1 to 4 C- atoms, in a straight or branched chain, especially methyl- or methoxy groups.

The phenoxy groups can contain substituents, such as Cl- or Br- or the above mentioned substituents, such as alkyl groups. The substituents of the benzene ring of the phenoxy group can be similar or different to the substituents of the benzene ring shown in the formula.

In particular, the following benzylhalides are considered nuclearly substituted: benzylchlorides and/or -bromides, showing an extra —$CH_2$—X substituent in o-, m- or p- position, i.e., p-, m-, or o- xylylenedichloride and/or -dibromide. Furthermore, there are such which show in addition to the —$CH_2$—X— substituent one or more substituents in the benzene ring, i.e., Cl- or Br- substituents, such as tetrachloroxylylenedichloride, the corresponding monochloro-dichloro-and trichloroxylylenedichlorides as well as the corresponding dibromides, alkyl-substituted xylylenedihalides, as i.e., $C_1$ to $C_4$-dialkyl-substituted xylylenedihalides, such as dimethyl- or diethylxylylenedihalides as well as the corresponding hydroxy-substituted xylylenedihalide like mono- and dihydroxy-xylylenedihalides.

Other nuclear-substituted chlorides or bromides capable of being reacted according to the invention are benzylhalides which in o- and/or m- and/or p- position in reference to the —$CH_2$—X group contain Cl- or Br- substituents and/or alkyl groups, like methyl- or alkoxy groups, like methoxy. In particular, there should be named: o- or m- or p- methylbenzylchloride, o- or m- or p- phenoxybenzylchloride, o- or m- or p- chlorobenzylchloride, o- or m- or p- bromobenzylchloride, 2,4-dimethylbenzylchloride, o- or m- or p- hydroxybenzylchloride, o- or m- or p- methoxybenzylchloride, o- or m- or p- nitrobenzylchloride or o-, or m- or p-cyanobenzylchloride, trichloro- or tribromo benzylchloride, tetrachlorobenzylchloride, tetrabromobenzylchloride, pentabromobenzylchloride, pentachlorobenzylchloride etc., as well as the corresponding bromides of the mentioned compounds.

The alkali metal and alkaline earth formates to be used according to the invention are namely sodium formate, potassium formate, magnesium formate, calcium formate, while in principle the formates of all other alkali metal > or alkaline earth metals can be employed as reactants. Sodium formate is preferred.

According to the inventive process, the conversion of the formate with the benzyl chloride occurs in the heterogenous phase. The formate should not be used in too coarse a form, since this would decrease the speed of conversion. Excessively fine grained formate may produce filtration difficulties when the resulting inorganic halide should be separated in solid form from the developed benzyl formate after the conversion with benzylhalide. Suitable grain size ranges are i.e. 0.025 to 0.5 mm.

The alkali metal and alkaline earth metal formates are employed in the quantity of 1 stoichiometric equivalent per equivalent benzylhalide stoichiometrically required for the complete process of the reaction. Perferably, one works with surplus quantities of the formate. The stoichiometric equivalent portion of benzylhalide to alkali metal, as well as alkaline earth formate, is generally 1:1-1.5. Preferably, one works with a slight stoichiometric excess represented by 1:>1 to 1:1.1.

Suitable catalysts for the reaction of benzylhalide with the formate are tertiary amines, tertiary phosphines, quaternary ammonium salts and quaternary phosphonium salts.

Homogeneous and heterogeneous tertiary amines are suitable with aliphatic, cycloaliphatic or aromatic radicals or heterocyclic tertiary amines.

Suitable tertiary amines with aliphatic radicals are, i.e., trimethylamine, triethylamine, tripropylamine, triisopropylamine, tri-prim.-n-butylamine, as well as their isomers, monoethyldiisopropylamine, N,N,N'N'-tetramethylethylenediamine, for instance, substituted tertiary, aliphatic diamine, like tri-($\beta$-ethoxyethyl)-amine, dimethyl- aminoacetonitrile, N,N-Di-n-butyl aminoacetonitrile, N,N-diisopropyl aminoacetonitrile, N-n-butyl-N-methyl aminoacetonitrile, N,N-diisobutyl aminopropionitrile, $\beta$-dimethyl aminopropionitrile, p-N,N-dimethylaminobenzonitrile.

For example, an amine with cycloaliphatic radical is dimethylcyclohexylamine.

Suitable amines with aromatic radicals are, i.e., N,N-dialkylaniline (N,N-dimethylaniline, N,N-diethylaniline, etc.), benzyldimethylamine, p-nitrophenyl-di-n-butylamine, N,N,N'-tetramethyl benzidine etc.

Suitable heterocyclic tertiary amines are the following:

hexamethylene tetramine, N-alkyl- as well as N-arylmorpholine, like N-n-butylmorpholine, N-phenylmorpholine, N-(p-methylphenyl-) morpholine, morpholino acetic acid-morpholide, N-aryl or N-alkyl-tetrahydroquinoline, or -tetrahydroisoquinoline, like N-n-propyltetrahydrozuinoline, N-phenyl-tetrahydroisoquinoline, i.e. N-alkyl- and N-arylpyrrolidine and their derivatives, i.e., N-methylpyrrolidine, N-n-butyl-pyrrolidine, N-phenylpyrrolidine etc. Other aromatic tertiary amines are pyridine, isoquinoline, pyrazine, oxazine, quinazoline, oxazol, oxdiazol, etc.

Especially suitable for the execution of the presented invention are tertiary amines with aliphatic radicals up to $C_4$, i.e., triethylamine, tributylamine triethylenediamine, as well as hexamethylenetetramine, dimethylaniline, N-methylmorpholine. Triethylamine is preferred.

Tertiary aliphatic phosphines are i.e., trimethylphosphine, triethylphosphine, tributylphosphine, trioctylphosphine, triisopropylphosphine.

Tricyclohexylphosphine is a phosphine with cycloaliphatic radicals.

Suitable phosphines with aromatic radicals are triphenylphosphine, tri-(4-methyl-phenyl)- phosphine, dimethyl-phenyl-phosphine, isopropyl-diphenylphosphine, carbethoxymethyl-diphenyl-phosphine, tribenzylphosphine, 1-phenyl-phospholane and 1-phenyl-phosphorinane.

Especially suitable for the execution of the present invention are tertiary phosphines with aliphatic radicals up to $C_4$, i.e. triethylphosphine or dibutylphosphine or others with aromatic radicals like triphenylphosphine and tribenzylphosphine. Tribenzylphosphine is preferred.

For the execution of the procedure according to the presented invention, all ammonium-halides derived through quaternization of the above-mentioned tertiary amines and tertiary phosphines with aliphatic $C_1$ up to $C_4$-alkylhalides or benzylhalides can be used as quaternary ammonium salts or phosphonium salts.

Tetracethylammoniumchloride, methyl-tricaprylammoniumchloride, tetrabutylammoniumchloride, trimethylbenzylammoniumchloride, triethylbenzylammoniumchloride, N-benzylpyridiniumchloride, triphenylmethylphosphoniumbromide and triphenylethylphosphoniumbromide have been found especially suitable.

Fundamentally, mixtures of the above-mentioned tertiary amines, tertiary phosphines quaternary ammonium slats and quaternary phosphonium salts are suitable catalysts for the conversion.

Tertiary amines, phosphines ammonium- or phosphonium salts used as catalysts are admixed in quantities of 0.1 to 10 parts by weight, preferably 0.5 to 5 parts by weight per 100 parts by weight of benzylhalide.

In general, the conversion takes place within a temperature range of 100° to 250° C., preferably between 110° and 200° C.

Preferably, the conversion is carried out at normal pressure, while, basically, one could work at elevated pressure, i.e., in an autoclave.

The trans-esterification of the benzylformate is carried out at elevated temperatures. Preferably, one works at boiling temperature of the reaction mixture, preferably in such a way that the formic acid ester developed from the admixed alcohol is continuously distilled from the reaction mixture during the trans-esterification process. Generally the trans-esterification can take place at temperatures between 30° and 250° C., preferably 50° to 200° C.

Primary or secondary aliphatic or cyclophatic univalent alcohols are admixed for esterification of the benzyl formate, i.e., $C_1$-up to $C_8$ alcohols.

Univalent alcohols are: methanol, ethanol, n-propanol-, n-butanol, amylalcohol, isopropanol, and cyclohexanol.

Primary or secondary aliphatic alcohols are favored, with preference given to those which have a low molecular weight, because at equal molar ratio of benzyl formate and alcohol, the higher is the weight concentration of benzyl formate in the reaction mixture, the lower is the molar weight of the alcohol. After complete trans-esterification, the weight concentration of the developed benzyl alcohol rises accordingly. Preferred for use are methanol, or ethanol or n-prim. butanol is isopropanol, especially methanol.

The alcohols are admixed at the least in the stoichiometrically necessary amount of 1 equivalent per formoxymethyl group, preferably in excess thereof. In general, the equivalent ratio 1:1 to 1:25, preferably 1:125 to 1:12 is used.

During trans-esterification, formic acid esters develop as valuable by-products, which are used as commercial solvents and as intermediates in synthesis.

According to the inventive process, acidic, basic or neutral compounds are admixed as esterification catalysts.

All mineral acids, e.g., oxo-acids, such as nitric acid, sulfuric acid, phosphoric acid, or hydrochloric acid are suitable as acidic catalysts, as well as carboxylic acids, especially formic acid and acetic acid. Mineral acids as well as carboxylic acids are admixed preferably as aqueous solutions of a concentration of, for example, 20 weight percent to 60 weight percent.

When using acidic esterification catalysts, the alcohols used for trans-esterification can contain water, which partially affects the trans-esterification in a favorable way. The water content of the trans-esterification mixture ranges between 2 to 80 volume percent, preferably between 5 to 50 volume percent.

As basic or neutral esterification catalysts one can use organo-oxy compounds, especially those of elements of the first, second and third group, as well as the fourth and fifth subordinate group of the Periodic System preferably of the elements Na, K, Mg, Ca, Al, Ti, Zr, V.

According to the invention, alcoholates of primary, secondary, or tertiary aliphatic, cycloaliphatic or aralphatic univalent or bivalent alcohols, especially $C_1$ up to $C_8$ alcohols, or phenolates wherein the metal component consists of a metal from the first to third group of the Periodic System can be used. The preferred metal component is sodium or potassium.

The preferred alcohol component corresponding to an alcoholate is an univalent $C_1$ to $C_4$ alcohol, preferably a primary or secondary alcohol, such as methanol, ethanol, propanol, isopropanol, or one of the isomeric primary or secondary butanols.

The alcoholates are preferably those based on the alcohols which are used for the esterification of benzyl formate. The alcoholates of benzyl alcohol and of the xylyleneglycols are also quite suitable with bivalent alcohols, mono-as well as di-alkali metal glycolates can be employed. Suitable phenolates are, e.g., those of the phenyl, cresol, salicyclic aldehyde or hydroxy benzoic acids.

Neutral catalysts useful in the invention are the esters of metallic acids of the elements of the fourth and fifth subordinate group of the Periodic System, especially that of titanium. Especially suitable is tetra-n- prim. -butyltitanate.

Acidic and basic esterification catalysts are admixed in quantities of 0.01 to 10 parts by weight, preferably 0.05 to 5 parts by weight. Neutral catalysts are admixed in quantities of 0.01 to 5 parts by weight, preferably 0.02 to 3 parts by weight per hundred parts by weight of benzyl formate.

When using alcoholates, phenolates or metallic acid esters as esterification catalysts, the univalent primary or secondary alcohols admixed to the trans-esterification reaction must be free of water or substantially free of water so that the same is not present in an amount of more than 8 weight percent. Appropriately, the water content of the trans-esterification mixture should not exceed 4 weight percent.

Preferred esterification catalysts are the alkali metal alcoholates especially sodium methylate.

The process of the invention is carried out as follows: the benzylhalide and the alkali metal or alkaline earth metal formate are placed into a reactor of stoichiometric ratio of preferably 1:>1 to 1.1 and, in a given instance, after melting the benzylhalide, the reaction mixture is vehemently agitated, generally by stirring in such a way that suspension of the formate occurs within the liquid benzylhalide.

The catalyst is introduced in portions into the suspension which is heated appropriately but not substantially above the melting point of the benzylhalide. In the case where lightly volatile amines like triethylamine are used, the reactor should be equipped with a reflux cooler when working under normal pressure, in order to prevent the escape of amine.

In general, the conversion to benzyl formate takes place in the temperature range of 100° to 250° C., preferably between 110° and 200° C.

The quantitative extent of conversion during the process can be easily determined by extracting crystalline portions from the hot suspension, and determining their residual formate portion through manganometric titration according to Blackadder (F. P. Tradwell, Handbook for Analytical Chemistry, 1949, pg. 536).

During the conversion, special protective gases are, apparently, unnecessary. Their absence does not affect reaction-speed, conversion or product quality.

After completing the reaction, a suspension of inorganic halide occurs in the benzyl formate from which the inorganic halide is separated through filtration or hydroextraction at temperatures above the solidification point of the benzyl formate.

The separation of the inorganic halide can be achieved in an advantageous manner, for instance, by using a submersible suction strainer or through hydroextraction in a heated filtration centrifuge.

The complete separation of benzyl formate without filtration or centrifugal residues is done by washing the same with organic solvents, such as acetone, methylisobutylketone or alcohols. It is advantageous to use alcohols which are intended to be used for the following trans-esterification of the benzyl formate.

Benzyl formates or-bisformates obtained in such a way may be admixed as such for the trans-esterification. In some instances, they are distilled for purification before esterification takes place, appropriately under vacuum. In general, purifying the benzyl formate before trans-esterification is not an absolutely necessary measure.

Preferably, the trans-esterification of the benzyl formates with primary and secondary alcohols is carried out at the boiling point of each corresponding reaction mixture, whereby the developed formic acid ester of the admixed alcohol is continuously distilled off, so that, after complete trans-esterification, the benzyl alcohols are found in solid form or in highly concentrated alcoholic solutions, from which benzyl alcohols can be separated through distillation of the alcoholic solutions.

The boiling points of the formic acid esters formed during esterification with the univalent primary or secondary alcohols are lower than the boiling points of the corresponding alcohols. Appropriately, the vaporization of the formic acid ester developed during trans-esterification takes place in a heated cooler whose cooling temperatures is regulated in such a way that the low boiling ester is distilled from the reactor, while the desired high boiling alcohol remains inside.

If one commences the trans-esterification with purified benzyl formates, the corresponding benzyl alcohols or glycols occur in high purity when the dissolved catalytic quantities of alcoholates or phenolates are neutralized with moist carbon dioxide and mineral acid catalysts are neutralized with basic agents, i.e., alkali metal hydroxides or carbonates, and, when the resulting inorganic salts are sucked off, before evaporating the alcoholic solutions. The metallic acid esters used as catalysts become hydrolyzed and the inorganic hydrolysis-products are separated in mechanical manner.

Volatile acids used as catalysts, such as formic acid or acetic acid can be distilled from benzyl alcohol solutions together with the excess alcohol.

According to the invention, the purification of the benzyl alcohols takes place preferably after the final phase of conversion, meaning after completion of esterification of benzyl formate and after evaporation of the residual alcohol.

Purification can be achieved through transcrystallization or distillation; distillation is the preferred method.

Before purification by distillation, is effected, acidic components of the reaction mixture must be taken up by neutralization with a basic agent, i.e., an alkali metal hydroxide, carbonates or bicarbonates, in order to prevent the formation of benzyl ethers or condensation products.

Especially suitable for the purification of benzyl alcohols is the method of vacuum distillation.

According to the invention, alcohol yields of up to 99% can be obtained when using benzyl chlorides. When using benzyl bromides the yields are lower.

The inventive process can also be carried out as "one pot" process where the mixture of benzyl formate and halide is not separated after the first conversion step, but is directly connected with the trans-esterification and only after completion of the second processing step is separation of inorganic halide from the alcoholic benzyl alcohol solution carried out.

According to the invention, the separation of benzyl alcohols is carried out in a manner described above.

According to the invention, the preferred form of carrying out the invention resides in effecting the separation of inorganic halide after completing of the reaction of benzylhalide with alkali metal or alkaline earth formate.

According to the invention, the admixed benzylhalides can be produced either through chlorine or bromine ethylation of benzene (compare, i.e., R. C. Fuson and C. H. McKeever, Org. Reactions I (1947) page 63) or through side chain chlorination or -bromination of toluene or toluenes substituted in the benzene ring (compare, i.e., Houben-Weyl, Method of Organic Chemistry, vol. V/3 (1962) page 736 and vol. V/4 (1960).

Compared to other syntheses, the inventive process has the following advantages:

1. The conversion of the benzylhalides with an alkali or alkaline earth formate takes place directly in mass, whereby the available reaction space of the reactor is used to its optimum.
2. As shown in the examples, the conversion takes place under normal pressure within a short time span and with high yields of benzyl formates.
3. The inorganic halide developed as by product is easily separated from the benzyl formates.
4. When trans-esterifying benzyl formates with alcohols, the benzyl alcohols are obtained in substantial quantities or as concentrated alcoholic solutions. The benzyl alcohols can be isolated without expensive extraction procedures by evaporation of large quantities of solvent. In this way, a high volume-time-yield can be achieved, and smaller reactors can be used.
5. During esterification, commercially valuable formic acid esters are obtained as by products which are used as solvents, insecticides and intermediate products for syntheses.

In order to more fully illustrate the nature of the invention and in a manner of practicing the same, the following examples are presented:

EXAMPLE 1

140.5 g p-methylbenzylchloride (1 mol) and 74.8 g sodium formate (1.1 mols) were placed into a four necked column, equipped with a reflux cooler, thermometer, dropping funnel and agitator; the mixture was heated to 80° C. and 1.7 g (0.017 mols) of triethylamine was dripped into the reaction mixture during agitation, whereby the temperature of the column content was raised to 150° C.

After two hours, the content of the column was cooled down to 50° C., the liquid phase was separated from the solid phase by filtration via a submersible suction strainer, the filtration residue was washed twice with 100 ml acetone each, the solvent was distilled off the washing solution and the vaporization residues were combined with the filtrate, which amounted to 151 g of the above reaction product.

By determining the residual formate content in the filtration residue (according to Blackadder) a formate consumption of 0.99 mols had occured, corresponding to a p-methylbenzylchloride conversion of 99%.

151 g of the oily reaction product were heated under reflux with 150 ml methanol (3.7 mols) containing 1 g sodium methylate (0.019 mol). The temperature of the cooling water was regulated at 32° C. The methyl formate was distilled off overhead from the cooler (boiling-point: 32° C.) and was led via a mounted distillation bridge through an intensive cooler and collected in a receiver.

After 35 minutes, the distillation was completed. For the separation of the remaining methyl formate, the cooling-water temperature of the reflux cooler was raised to 42° C. The distillate weighed 64 g and consisted of 96% methyl formate, which was obtained through distillation in pure form.

From the content which remained in the reaction-flask, methanol was distilled off and the residue was subjected to another distillation under reduced pressure.

115.9 g p-methylbenzyl alcohol were distilled at 103.5°–105° C. and 12 mm, which amounts to a yield of 95%, in response to p-methylbenzylchloride. The melting point ranged between 58°–59° C.

EXAMPLE 2a to 2c

Procedures were used as in Example 1, with the exception that instead of using triethylamine as a catalyst for the conversion of p-methylbenzylchloride and sodium formate, catalysts mentioned in Table 1 were used.

Yields for p-methylbenzylchloride and p-methylbenzyl alcohol are shown in Table 1.

TABLE 1

| Ex. | Catalyst | Mols | Reaction-time (h) | p-Methyl-benzyl-chloride conversion (%) | p-Methylbenzyl-alcohol yield (g/%) | melting point (°C.) |
|---|---|---|---|---|---|---|
| 2a | trimethyl benzyl-ammonium-chloride | 0.20 | 2 | 99.1 | 117.1/96 | 58–59 |
| 2b | triphenyl-phosphine | 0.03 | 4 | 98.3 | 114.7/94 | 57.5–58.5 |
| 2c | triphenyl-ethyl-phosphonium-bromide | 0.02 | 2.5 | 98.5 | 115.9/95 | 58–59 |

EXAMPLE 3

Analogous to the conversion carried out in Example 1, potassium formate was used instead of sodium formate.

In the presence of 2.0 g (0.02 mol) triethylamine, 140.5 g p-methylbenzylchloride was reacted with 92.5 g potassium formate (1.1 mols) at 150° C. After 2.5 hours, the p-methylbenzylchloride conversion amounted to 99.5%.

Through esterification of the resulting p-methylbenzyl formate with 90 ml methanol in the presence of 1 g sodium methylate, 113.5 g p-methylbenzyl alcohol were received at a melting point of 58° C., corresponding to a yield of 93%, based on the reacted p-methylbenzylchloride.

EXAMPLES 4a to 4i

According to Example 1, each 1 mol of the benzylhalide substituted in the benzene ring in Table 2 and 74.8 g sodium formate were reacted in the presence of a catalyst to the corresponding formates which were distilled off under reduced pressure, and, according to Example 1, were esterified to the corresponding benzyl alcohol employing methanol and an esterification catalyst.

TABLE 2

| Example | Benzylhalogenide Chem. term | (g) | Catalyst (Mol) | Formiate % | Methanol (ml/Mole) | Esterification catalyst | (Mol) | Benzylalcohol Yield (g/%) | Melt. Pt. (°C.) | Boil. Pt. (°C.) |
|---|---|---|---|---|---|---|---|---|---|---|
| 4 a | m-Methyl-benzylchloride | 140.5 | TMBAC* (0.017) | 97.3 | 81/2 | K-tert.-Butylate | 0.025 | m-Methyl-114.8/94.1 | <20 | 104–105 (12 mm) |
| 4 b | o-Methyl-benzylchloride | 140.5 | TMBAC* (0.020) | 96.9 | 162/4 | K-tert.-Butylate | 0.015 | o-Methyl-115.9/95.0 | 35–36 | 105–107 (12 mm) |
| 4 c | m-Phenoxy-benzylchloride | 218.5 | TMBAC* (0.021) | 94.3 | 101/2.5 | Mg-ethylate | 0.015 | m-Phenoxy-182.4/91.2 | <20 | 142–144 (0.6 mm) |
| 4 d | o-Chlor-benzylchloride | 161 | TEA** (0.041) | 94.0 | 61/1.5 | Mg-ethylate | | o-Chlor-129.2/91.0 | 67–68 | 114–116 (13 mm) |
| 4 e | p-Nitro-benzylchloride | 171.5 | TEA** (0.035) | 95.5 | 81/2 | Al-iso-propylate | 0.010 | p-Nitro-140.9/92.1 | 93 | 184–185 (12 mm) |
| 4 f | 2,4-Dimethyl-benzylchloride | 155.5 | TPP*** (0.032) | 97.3 | 101/2.5 | Butyl-titanate | 0.011 | 2,4-Dimethyl-126.8/93.2 | 28–29 | 120–121 (13 mm) |
| 4 g | p-Hydroxy-benzylchloride | 142.5 | TMBAC* (0.020) | 96.5 | 202/5 | Na-Phenolate | 0.031 | p-Hydroxy-116.9/94.3 | 124 | — |
| 4 h | p-Methyl-benzylchloride | 140.5 | TEA** (0.024) | 97.5 | 202/5 | Na-p-Methyl-benzylate | | p-Methyl-115.9/95.0 | 58.5–59.5 | 107–108 (14 mm) |
| 4 i | p-Cyan-benzylchloride | 151.5 | TMBAC* (0.025) | 93.8 | 202/5 | K-tert.-Butylate | 0.031 | p-Cyan-120.4/90.5 | 132.5–134 | — |

*TMBAC = Trimethylbenzylanmoniumchloride
**TEA = Triethylamine
***TPP = Triphenylphosphine

EXAMPLES 5a to 5d

According to Example 1, 562 g p-methylbenzylchloride (4 mols) were reacted with 299.2 g sodium formate (4.4 mols) in the presence of 11.2 g hexamethylenetetramine (0.08 mols) at 140° C. After 3 hours reaction time, the methylbenzylchloride conversion amounted to 99.3%.

The quantity of the reaction product freed from sodium chloride and excess sodium formate amounted to 600.5 g. Each 150.1 of this product was esterified with 4 mols of alcohols listed in Table 3, in the presence of 0.025 mols of the corresponding sodium alcoholate. The trans-esterification time amounted to 1.25 hours. The formic acid esters which had developed in the meantime were purified through distillation.

TABLE 3

| Example | alcohol | Boiling point (°C.) | Quantity (ml) | Cooling water temp. | Formic acid ester CP (°C.) | Formic acid ester Yield (%) | p-Methyl-benzyl Yield | p-Methyl-benzyl Melting point |
|---|---|---|---|---|---|---|---|---|
| 5a | methanol | 65 | 162 | 32 | 32 | 98 | 95.1 | 58.5–59 |
| 5b | ethanol | 78.5 | 234 | 53 | 54 | 97 | 96.1 | 57–58 |
| 5c | n-prim.-butanol | 117.7 | 366 | 106 | 97 | 97* | 94.5 | 57.5–58.5 |
| 5d | iso-propanol | 82.3 | 306 | 71 | 71 | 96 | 95.0 | 57.5–58.5 |

*in azeotrope with butanol

EXAMPLE 6

According to Example 1, 140.5 g p-methylbenzyl-chloride (1 mol) were reacted with 74.8 g sodium formate (1.1 mols) and 4 g trimethylbenzylammoniumchloride (0.22 mols) at 140° C.

After two hours of reaction time, the conversion amounted to 99.5%. The reaction product, separated from the sodium chloride, was distilled under a water jet vacuum. At 12 mm and 97° to 98° C. 145.5 g p-methylbenzyl formate were recovered corresponding to a yield of 97%.

145.5 g p-methylbenzyl formate were heated for 2 hours under reflux with 166 ml methanol, 50 ml water and 10 ml formic acid while maintaining the colling-water temperature at 32° C. whereby methyl formate was distilled off. The condensate weighed 62 g. 56 g methyl formate corresponding to a yield of 96.2% were obtained through distillation.

Methanol and water were distilled off from the methanol/water-p-methylbenzyl alcohol which had remained in the reaction flask. The colorless product had a melting point of 58°–59° C. and weighed 115.3 g, corresponding to a yield of 94.5% based on the admixed p-methylbenzylchloride.

EXAMPLE 7

According to Example 1, 175 g o-xylylenedichloride (1 mol) were reacted with 149.6 g sodium formate (2.2 mols) and 3.5 g triethylamine (0.035 mol) at 150° C.

After 2.5 hours reaction time, the conversion of o-xylylenedichloride amounted to 99.3%. The conversion product, freed of sodium chloride, was subjected to a vacuum distillation. At 0.2 mm, 187.2 g o-xylyleneglycolbisformate were recovered at a temperature of 99°–103° C., corresponding to a yield of 96.5%. 187.2 g o-xylyleneglycolbisformate were heated with 317 ml methanol and 2.2 g sodium methylate under reflux for 2 hours and at a temperature of 32° C., whereby methyl formate was distilled off. The condensate weighed 125 g. 112 g methyl formate were obtained through distillation corresponding to a yield of 97%.

Methanol was distilled off from a mixture of methanol and o-xylyleneglycol which had remained in the reaction flask. The remaining residue was dried over calcium oxide (burnt lime). The colorless product had a melting point of 63°–64° C. and weighed 130.4 g, corresponding to a yield of 94.5%, based on the admixed o-xylylenedichloride.

EXAMPLE 8

According to Example 1, 244 g of 2,5-dichloro-1,4-bis-chloro-methylbenzene (1 mol) were reacted with 149.6 g sodium formate and 4.5 g trimethylbenzylammoniumchloride (0.024 mol) at a temperature of 150° C.

After 3 hours reaction time, the conversion amounted to 99.6%.

The reaction products was trans-esterified with 200 ml methanol in the presence of 1.5 g sodium methylate. After transcrystallization, 190.4 g of 2,5-dichloro-1,4-bis-hydroxymethylbenzene were obtained at a flame point of 201°–202° C., corresponding to a yield of 92%, based on the admixed 2,5-dichloro-1,4-bis-chloromethylbenzene.

EXAMPLE 9

175.1 g p-xylylenedichloride (1 mol) and 146.2 g sodium formate (2.15 mols) free of water and in powder form were placed into a 4 necked column, equipped with reflux cooler, thermometer, dropping funnel and agitator, and the mixture was heated to 110° C.

After complete fusion of the p-xylylenedichloride, the agitator was turned on, 1.7 g (0.017 mols) triethylamine was dripped into the reaction mixture and the entire column content was heated to 150° C. under heavy agitation.

After 1.5 hours, the flask content was cooled to 115° C., the liquid phase was separated from the solid phase through filtration over a submersible suction filter strainer, the filtration residue were washed twice with 100 ml methylisobutylketone each, the solvent was evaporated from the washing solution and the evaporization radicals were combined with the filtrate which amounted to 195.5 g. The product has a melting point of 82° to 84° C.

Through determination of the residual formate content in the filtration residue (according to Blackadder) a formate consumption of 1.98 mols resulted, corresponding to a p-xylylenedichloride conversion of 99.0%.

The product, melting around 83° to 84° C., was heated with 150 ml methanol (3.7 mols) which contained 0.54 g sodium methylate (0.01 mols), whereby the temperature of the cooling water was regulated at 32° C.

Methyl formate (boiling point 32° C.) was distilled off overhead of the cooler, and was led via an attached distillation bridge through an intensive-cooler and collected in a receiver.

After 0.5 hours, the distillation was completed. In order to extract the remaining methyl formate, the temperature of the cooled reflux unit was raised for a short time to 40° C.

The distillate weighed 128.2 g and consisted of 96% methyl formate which was obtained in pure form through a Vigreux column.

The excess methanol was evaporated from the contents which had remained in the reaction flask, and the residue was subjected to distillation under reduced pressure. 134.4 g p-xylyleneglycol distilled at 0.5 Torr and 140° to 142° C. which corresponds to a yield of 97.4%, based on p-xylylenedichloride.

EXAMPLES 10 and 11

Procedures were carried out as in Example 9 with the exception that instead of using triethylamine as catalyst for the conversion of p-xylylenedichloride and sodium formate, 3.5 g tri-n-prim.-butylamine (0.02 mol) and 2.8 g (0.02 mol) hexamethylenetetramine were admixed.

Xylylenedichloride conversion and xylyleneglycol yields can be read in Table 1.

TABLE 1

| Ex. | Tert. Amine | Xylylenedichloride conversion | Reaction time | Xylyleneglycol yield g/% | Melting Point °C. |
|---|---|---|---|---|---|
| 10 | tri-n-prim. butylamine | 94.3 | 1.25 | 128.1/ 92.8 | 115–116 |
| 11 | hexamethylene | 96.3 | 1.75 | 131.0/ 94.9 | 114.5–115.5 |

EXAMPLE 12

Analogous to the conversion carried out in Example 9, potassium formate was used instead of sodium formate.

In the presence of 1 g triethylamine, 88.6 g (98.8%) p-xylylenedichloride (0.5 mols) were reacted with 92.5 g potassium formate (1.1 mols) at 140° C. After 2 hours, the p-xylylenedichloride conversion amounted to 99.2%.

Through trans-esterification of the obtained p-xylyleneglycol-bis-formate (melting point: 83.5°–84.5° C.) with 90 ml methanol in the presence of 0.27 g Na-methylate, 66.3 g xylyleneglycol resulted in a yield of 96% (based on admixed p-xylylenedichloride). The melting point ranged between 115° and 116° C.

EXAMPLES 13a through 13h

According to Example 9, 1.424 kg p-xylylenedichloride (8 mols) and 1.156 kg sodium formate (17 mols) were reacted in the presence of 26.6 g (0.26 mols) triethylamine at 150° C. After 2 hours reaction time, the p-xylylenedichloride conversion amounted to 99.5%.

The reaction product, freed from sodium chloride and excess sodium formate weighed 1.576 kg.

Each 197.9 g of this product was esterified with methanol in the presence of catalysts listed in Table 2. The trans-esterification time was 1 hour.

TABLE 2

| Ex. | Methanol ml/Mols | Catalyst | Moles of catalyst | Xylyleneglycol yield (%) | Melting Point °C. |
| --- | --- | --- | --- | --- | --- |
| 13a | 161.5/4 | aluminum isopropylate | 0.012 | 95.5 | 115–116 |
| 13b | 182/4.5 | sodium phenolate | 0.015 | 96.3 | 114.5–115.5 |
| 13c | 150/3.7 | magnesium methylate | 0.020 | 94.8 | 115–116 |
| 13d | 150/3.7 | potassium tert. butylate | 0.05 | 96.1 | 115–116 |
| 13e | 323.0/8.0 | n-prim.-tetrabutyl-titanate | 0.002 | 93.0 | 114.5–115.5 |
| 13f | 161.5/4 | sodium benzylate | 0.02 | 96.8 | 115–116 |
| 13g | 150.0/3.7 | disodium-p-xylyleneglycolate | 0.018 | 96.6 | 115–116 |
| 13h | 182.0/4.5 | monosodium p-xylyleneglycolate | 0.025 | 95.8 | 115–116 |

EXAMPLES 14a to 14d

According to Example 9, 700.4 g p-xylylenedichloride (4 mols) were reacted with 598.4 g sodium formate (8.8 mols) in the presence of 11.2 g hexamethylenetetramine (0.08 mol) at 150° C.

After 2 hours reaction time, the p-xylylenedichloride conversion amounted to 98.3%.

The quantity of the reaction product, freed from sodium chloride and from excess sodium formate, amounted to 777.0 g.

Each 194.3 g of this product was trans-esterified with 5 mols of the alcohols listed in Table 3 in the presence of 0.01 mol of the corresponding sodium alcoholate. The esterification time amounted to 1.5 hours. The developed formic acid esters were purified by distillation.

TABLE 3

| Example | Alcohol | Boiling point °C. | Quantity ml | Cooling water temp. °C. | Formic acid ester BP °C. | Formic acid ester yield % | Xylylene glycol yield | Melting Point |
| --- | --- | --- | --- | --- | --- | --- | --- | --- |
| 14a | methanol | 65 | 202 | 32 | 32 | 98 | 96.1 | 115–116 |
| 14b | ethanol | 78.5 | 292 | 53 | 54 | 97 | 95.5 | 115.5–116.5 |
| 14c | n-prim.-butanol | 117.7 | 458 | 106 | 197 | 97* | 95.8 | 115–116 |
| 14d | iso-propanol | 82.3 | 383 | 71 | 71 | 98 | 94.9 | 115–116 |

*in azeotrope with butanol

EXAMPLE 15

According to Example 9, 350.2 g p-xylylenedichloride (2 mols) were reacted with 299.2 g sodium formate (4.4 mols) in the presence of 4.3 g triethylamine (0.04 mol) at 146° C. After 2 hours reaction time, the p-xylylenedichloride conversion amounted to 99.0%.

The developed sodium chloride was separated by filtration from the reaction mixture which was cooled down to 110° C., and the filtration residue was washed twice each with 200 ml methylisobutylketone, after vaporization of the solvent from the washed solution, the evaporated residues were combined with the filtrate and the entire mixture subjected to a distillation under reduced pressure.

At 1.4 mm and 123° to 124° C., 380.2 g p-xylyleneglycol-bis formate distilled off, corresponding to a yield of 98.0%. The melting point was 85° C.

380 g p-xylyleneglycol-bis formate (1.96 mols) were heated for 2 hours under reflux with 323 ml methanol and 100 ml water (8 mols) in the presence of 10 ml formic acid at a cooling water temperature of 32° C., whereby methyl formate distilled off. The condensate weighed 261.1 g and contained 8% methanol. Through distillation over a Vigreux-column, 235.3 g pure methyl formate were obtained, corresponding to a yield of 98.0%.

Water and residual formic acid were distilled off from the aqueous methanolic p-xylyleneglycol solution which had remained in the reaction flask, and the residues were dried in a vacuum at 80° C. The completely colorless product exhibited a melting point of 115°–116° C. and weighed 265.5 g, corresponding to a yield of 96.2%.

EXAMPLE 16

According to Example 9, 645 g m-xylylenedichloride (3.68 mols) were reacted with 550 g sodium formate (8.1 mols) in the presence of 12.9 g triethylamine at 148° C. After 2 hours reaction time, the conversion of m-xylylenedichloride amounted to 98.5%.

The conversion product, separated from the sodium chloride and excess sodium formate, weighed 709 g and had a melting point of 32° C.

The m-xylyleneglycol-bis formate was heated for 1.5 hours under reflux at a cooling water temperature of 32° C. together with 742 ml methanol (18.4 mols) in which 0.45 g sodium were dissolved, whereby methyl formate distilled off. The condensate weighed 481 g and consisted of 92% methyl formate.

Methanol was evaporated from the methanolic m-xylyleneglycol solution left over in the reaction flask, and the residue was distilled under reduced pressure.

At 0.22 Torr and 124°–126° C., 492.1 g m-xylyleneglycol was obtained, corresponding to a yield of 97.4%. Its melting point was 55° to 56° C.

EXAMPLE 17

According to Example 1, 87.5 g m-xylylenedichloride (0.5 mols) were reacted with 71.6 g calcium formate (0.55 mols) in the presence of 0.9 g triethylamine for 1.5 hours at 152° C.

After this amount of time had passed, the conversion of m-xylylenedichloride amounted to 98.6%.

The reaction product, separated from the calcium chloride and the excess calcium formate, weighed 97.2 g.

The m-xylyleneglycol-bis formate was heated for one hour under reflux at a cooling water temperature of 54° C. with 175 ml ethanol (3 mols) containing 0.5 g calcium ethylate, whereby ethyl formate mixed with ethanol distilled off. 83.2 g condensate were weighed out, containing 11% ethanol. By means of fractional distillation, 72.2 g ethyl formate were obtained, corresponding to a yield of 97.5%.

The solvent was distilled off from the solution of m-xylyleneglycol remaining in the reaction flask, and the residues were subjected to a distillation under reduced pressure.

At 0.2 Torr, 66.5 g distilled off, corresponding to a yield of 96.4%. Its melting point was around 55° to 56° C.

EXAMPLE 18

In a four-necked column, equipped with reflux cooler, thermometer, dropping funnel and agitator, 175.1 g p-xylylenedichloride (1 mol) and 142.8 g sodium formate (2.1 mols) were reacted in the presence of 2.1 g triethylamine at 146° C. and under heavy agitation. After 2 hours of reaction time, the reaction mixture was cooled down to 90° C. and 350 ml water were added under continued agitation at 90° C.

After separation of the aqueous solution containing sodium chloride, the hot oil at 90° C. washed free of chlorides twice with 50 ml water of 90° C. The remaining oil solidified at 84° C.

After drying the disintegrated material under vacuum at 80° C., the weigh-out same amounted to 188.2 g.

202 ml (5 mols) of methanol were heated under reflux at a cooling water temperature of 32° C. in the presence of 0.65 g sodium methylate, whereby methyl formate distilled off. The condensate weighed 134.5 g and contained 12% methanol.

Excess methanol was evaporated from the methanolic p-xylyleneglycol solution remaining in the reaction flask, and the residues were distilled under reduced pressure.

At 0.5 Torr and 140°–142° C., 184.7 g xylyleneglycol distilled off, corresponding to a yield of 95.2%. The melting point was between 115.5° and 116.5° C.

COMPARATIVE EXAMPLE 87.5 g p-xylylenedichloride (0.5 mols) were mixed with 158.4 g sodium benzoate (1.1 mols). After heating to 110° C., a mixture developed incapable of being stirred. After admixing 1.7 g triethylamine, the reaction mixture was heated for 2 hours at 130° C. and was then stirred into water. According to analysis, the resulting solid oil consisted of 73% p-xylylenedichloride incapable of being reacted.

What is claimed is:

1. A process for preparing benzylalcohol or benzylalcohol having a substituent on the benzene ring which comprises:

A. Contacting a benzylchloride and/or bromide or a benzylchloride and/or bromide singularly or multiply substituted on the benzene ring which compound has the formula

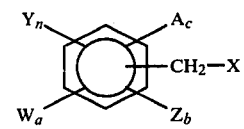

wherein
    Y = halogen and/or alkyl
    n = 0 to 5
    W = —CH$_2$—X
    a = 0 to 5
    Z = hydroxy or alkoxy
    b = 0 to 3
    A = nitro and/or nitrile
    c = o to 2 and a+b+n+c = 1 to 5, and X represents chlorine or bromine
    at a temperature of 100° to 250° C. with an alkali metal or alkaline earth metal formate such that said benzylchloride and/or bromide reacted is in the heterogeneous phase in the presence of a catalyst selected from the group consisting of tertiary amines, tertiary phosphines, quaternary ammonium salts and quaternary phosphonium salts and in the absence of a solvent to form benzylformate or a benzylformate which contains a substituent on the benzene ring; and B. Thereafter converting the so formed benzylformate or substituted benzylformate by means of a transesterification step to the corresponding alcohol by contacting the same with an alcohol in the presence of an esterification catalyst.

2. A process according to claim 1 wherein Y = halogen and/or alkyl of 1 to 4 carbon atoms, n is 0 to 2, a = 0 to 2, Z = hydroxy or C$_1$ to C$_4$ alkoxy b = 0 to 2.

3. A process according to claim 1 wherein the benzyl chloride and/or bromide reactant is a chloro, dichloro, bromo, methyl, dimethyl, methoxy, hydroxy or nitrobenzylchloride and/or bromide or an ortho, meta or para xylylenedichloride and/or xylylenedibromide.

4. A process according to claim 1 wherein the stoichiometric molar ratio of halogen methyl groups of the benzyl chloride and/or bromide reactant to formate is in the range of 1:1 to 1.5.

5. A process according to claim 4 wherein said stoichiometric ratio is 1:>1 than to 1.1.

6. A process according to claim 1 wherein said formate is sodium formate.

7. A process according to claim 1 wherein the benzyl chloride and/or bromide is reacted with the formate at a temperature in the range of 110° to 200° C.

8. A process according to claim 1 wherein the catalyst employed for reaction of the benzyl chloride and/or bromide with the formate is a tertiary amine.

9. A process according to claim 8 wherein said tertiary amine is triethylamine, tripropylamine, a tributylamine, dimethylaniline, N-methyl-morpholine, hexamethylenetetramine or triethylenediamine.

10. A process according to claim 9 wherein said tertiary amine is triethylamine.

11. A process according to claim 1 wherein the catalyst for the reaction of the benzyl chloride and/or bromide with the formate is a tertiary phosphine.

12. A process according to claim 11 wherein said tertiary phosphine is triethylphosphine, tributylphosphine, triphenylphosphine or tribenzylphosphine.

13. A process according to claim 12 wherein said tertiary phosphine is triphenylphosphine.

14. A process according to claim 1 wherein the catalyst employed for the reaction of the benzyl or chloride and/or bromide with the formate is a quaternary ammonium salt.

15. A process according to claim 14 wherein said quaternary ammonium salt is methyltricaprylylammonium chloride, a tetrabutylammonium chloride, trimethylbenzylammonium chloride or triethylbenzylammonium chloride.

16. A process according to claim 1 wherein the catalyst employed for reaction of the benzyl chloride and/or bromide with the formate is a quaternary phosphonium salt.

17. A process according to claim 16 wherein the quaternary phosphonium salt is triphenylmethylphosphonium bromide or triphenylethylphosphonium bromide.

18. A process according to claim 1 wherein the catalyst employed in the reaction of the benzyl chloride and/or bromide with the formate is employed in an amount of 0.1 to 10 parts by weight per 100 parts of benzylchloride and/or bromide reactant.

19. A process according to claim 18 wherein said catalyst is employed in an amount of 0.5 to 5 parts by weight per 100 parts of benzylchloride and/or bromide reactant.

20. A process according to claim 11 wherein in step B, the stoichiometric proportion of formoxymethyl groups to alcohol employed for the esterification is in the range of 1:1.2 to 25.

21. A process according to claim 20 wherein the stoichiometric proportion of formoxymethyl groups of the formate so formed in step A to alcohol employed in step B is in the range of 1:1.25 to 12.

22. A process according to claim 1 wherein the alcohol employed for trans-esterification in step B is a primary of secondary univalent alcohol.

23. A process according to claim 22 wherein said alcohol is methanol, ethanol, n-propanol, n-butanol, isobutanol, isopropanol or secondary butanol.

24. A process according to claim 1 wherein the trans-esterification of the benzyl formate or xylyleneglcolbisformate formed according to step A with the alcohol in step B is carried out at the boiling temperature of the reaction mixture.

25. A process according to claim 1 wherein the formic acid ester which forms as a result of contacting the formate formed in step A with alcohol according to step B is continuously distilled off from the trans-esterification reaction mixture.

26. A process according to claim 1 wherein the esterification of step B is carried out in the presence of an acid catalyst.

27. A process according to claim 21 wherein the acid catalyst is nitric acid, sulphuric acid, phosphoric acid, hydrochloric acid, formic acid or acetic acid.

28. A process according to claim 27 wherein said acid is in the form of an aqueous solution.

29. A process according to claim 1 wherein the esterification of step B takes place in the presence of an alcoholate.

30. A process according to claim 29 wherein the alcohol component of the alcoholate is derived from a primary, secondary or tertiary alcohol.

31. A process according to claim 30 wherein the alcohol component of the alcoholate, is methanol, ethanol, propanol, isopropanol or one of the isomeric butyl alcohols.

32. A process according to claim 1 wherein the trans-esterification of step B takes place in the presence of a phenolate.

33. A process according to claim 32 wherein said phenolate is derived from phenol, an ortho, meta or para cresol, salicylic aldehyde or an ortho, meta or para hydroxybenzoic acid ester.

34. A process according to claim 1 wherein the trans-esterification of step B is carried out in the presence of an alcoholate or phenolate of an alkali metal, alkaline earth metal or aluminium.

35. A process according to claim 34 wherein said alcoholate or phenolate is an alcoholate or phenolate of sodium, potassium, calcium or magnesium.

36. A process according to claim 1 wherein the catalyst employed in the trans-esterification step B is employed in an amount of 0.01 to 10 weight percent based upon the amount of benzyl formate in the reaction mixture.

37. A process according to claim 1 wherein the esterification catalyst is present in an amount of 0.05 to 5 weight percent.

38. A process according to claim 1 wherein the trans-esterification takes place in the presence of a metallic acid ester.

39. A process according to claim 38 wherein said metallic acid ester is a titanic acid ester.

40. A process according to claim 39 wherein said titanic acid ester is a tetrabutyltitanate.

41. A process according to claim 40 wherein said tetrabutyltitanate is tetra-n-prim.-butyltitanate.

42. A process according to claim 38 wherein said metallic acid ester is employed in an amount of 0.01 to 5 weight percent, based upon the amount of benzylformate in the reaction mixture.

43. A process according to claim 42 wherein said metallic acid ester is present in an amount of 0.02 to 3 weight percent, based upon the amount of benzylformate in the reaction mixture.

44. A process according to claim 26 wherein the trans-esterification is carried out in an aqueous alcoholic medium.

45. A process according to claim 44 wherein the amount of water in the aqueous alcoholic medium is 2 to 80 volume percent.

46. A process according to claim 45 wherein the amount of water in the aqueous alcoholic medium is 5 to 50 volume percent.

47. A process for preparing benzylalcohol or a benzylalcohol having a substituent on the benzyl ring which comprises:

A. Contacting a benzylchloride and/or bromide or a benzylchloride and/or bromide singularly or multiply substituted on the benzene ring which compound has the formula

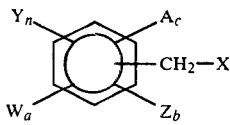

wherein
Y = halogen and/or alkyl
n = 0
W = —CH$_2$—X
a = 0 to 5
Z = hydroxy, alkoxy or phenoxy
b = 0 to 3
A = nitro and/or nitrile
c = 0 a+b+n+c = 1 to 5, and X represents chlorine or bromine
at a temperature of 100° to 250° C. with an alkali metal or alkaline earth metal formate such that said benzylchloride and/or bromide reacted is in the heterogeneous phase in the presence of a catalyst selected from the group consisting of tertiary amines, tertiary phosphines, quaternary ammonium salts and quaternary phosphonium salts and in the absence of a solvent to form benzylformate or a benzylformate which contains a substituent on the benzene ring; and B. Thereafter converting the so formed benzylformate or substituted benzylformate by means of a transesterification step to the corresponding alcohol by contacting the same with an alcohol in the presence of an esterification catalyst.

48. A process for preparing benzylalcohol or a benzylalcohol having a substituent on the benzene ring which comprises:

A. Contacting a benzylchloride and/or bromide or a benzylchloride and/or bromide singularly or multiply substituted on the benzene ring which compound has the formula

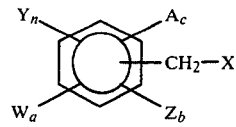

wherein
Y = halogen and/or alkyl
n = 0 to 2
W = —CH$_2$—X
a = 0 to 5
Z = hydroxy or alkoxy
b = 0 to 3
A = nitro and/or nitrile
c = 0 to 2 and a+b+n+c = 1 to 5, and X represents chlorine or bromine
at a temperature of 100° to 250° C. with an alkali metal or alkaline earth metal formate such that said benzylchloride and/or bromide reacted is the heterogeneous phase in the presence of a catalyst selected from the group consisting of tertiary amines, tertiary phosphines, quaternary ammonium salts and quaternary phosphonium salts and in the absence of a solvent to form benzylformate or a benzylformate which contains a substituent on the benzene ring; and B. Thereafter converting the so formed benzylformate or substituted benzylformate by means of a transesterification step to the corresponding alcohol by contacting the same with an alcohol in the presence of an esterification catalyst.

\* \* \* \* \*